United States Patent [19]

Baumann et al.

[11] Patent Number: 4,652,653

[45] Date of Patent: * Mar. 24, 1987

[54] PROCESS FOR THE PREPARATION OF β-(BENZOTHIAZOLYLTHIO)- AND β-(BENZIMIDAZOLYLTHIO)-CARBOXYLIC ACID DERIVATIVES

[75] Inventors: Marcus Baumann; Hans Bosshard, both of Basel; Hans Greuter, Gipf-Oberfrick, all of Switzerland

[73] Assignee: Ciba-Geigy Corporation, Ardsely, N.Y.

[*] Notice: The portion of the term of this patent subsequent to Sep. 16, 2003 has been disclaimed.

[21] Appl. No.: 731,252

[22] Filed: May 7, 1985

[30] Foreign Application Priority Data

May 11, 1984 [GB] United Kingdom ............... 8412065

[51] Int. Cl.$^4$ .................. C07D 277/74; C07D 235/28
[52] U.S. Cl. .................................. 548/171; 548/170; 548/327; 548/329
[58] Field of Search ............... 548/170, 171, 329, 327

[56] References Cited

U.S. PATENT DOCUMENTS 2,725,364  11/1955  Dazzi ............................ 260/30.2
3,161,495  12/1964  Miller ............................ 548/170

FOREIGN PATENT DOCUMENTS 0126030  11/1984  European Pat. Off. ............ 548/170

OTHER PUBLICATIONS

F. B. Zienty et al, J. Org. Chem., 27, 3140 (1962).
A. F. Halasa et al, J. Org. Chem., 36, 636 (1971).

Primary Examiner—Donald G. Daus
Assistant Examiner—Mary E. Ceperley
Attorney, Agent, or Firm—Luther A. R. Hall

[57] ABSTRACT

The reaction of 2-mercapto-benzothiazole or -benzimidazole with α,β-unsaturated carboxylic acid derivatives in a strongly acid reaction medium gives compounds of the formula I

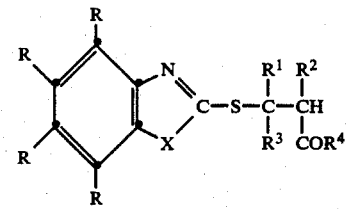

in which X is sulfur or NH, each radical R independently of one another is H, alkyl, halogenalkyl, alkoxy, alkylthio, alkylsulfonyl, phenyl, alkylphenyl, phenylalkyl, cycloalkyl, halogen, $NO_2$, CN, COOH, COOalkyl or a tertiary amino or carbamoyl group and $R^1$, $R^2$ and $R^3$ independently of one another are H, alkyl, halogenalkyl, hydroxyalkyl, alkoxyalkyl unesterified or esterified carboxyl or carboxylalkyl, carbamyol, carbamyolalkyl or unsubstituted or substituted aryl or aralkyl, or $R^1$ and $R^2$ together are straight-chain or branched alkylene, which can be substituted by 1 or 2 carboxyl groups, $R^4$ is unsubstituted or substituted amino, alkoxy, cycloalkoxy, aryloxy or aralkyloxy, or $R^2$ and $R^4$ together are $CH_2$—CO—O— or —$CH_2$CO—$NR^5$— or $R^3$ and $R^4$ together are —CO—O— or —CO—$NR^5$—, forming an anhydride or imide ring, wherein $R^5$ is unsubstituted or substituted alkyl, cycloalkyl, aryl, aralkyl or hydrogen.

13 Claims, No Drawings

PROCESS FOR THE PREPARATION OF β-(BENZOTHIAZOLYLTHIO)- AND β-(BENZIMIDAZOLYLTHIO)-CARBOXYLIC ACID DERIVATIVES

The present invention relates to a process for the preparation of esters, amides, imides and anhydrides of aliphatic or cycloaliphatic carboxylic acid derivatives which are substituted in the β-position by a heterocyclic mercapto radical, which comprises reacting an α,β-unsaturated carboxylic acid derivative with a heterocyclic mercaptan in an strongly acid medium.

The addition of mercaptans onto α,β-unsaturated acids and their derivatives is known in principle. However, it is usually carried out in a basic medium or using basic catalysts. It is assumed that the first step in this reaction consists of addition of the mercaptide anion onto the β-carbon atom of the carboxylic acid. F. B. Ziently et al. (J.Org.Chem. 27 (1962), 3140) described the addition of various thiols onto maleic anhydride under basic catalysis. These authors comment that the addition under free radical catalysis gives only moderate yields, and that Lewis acids have no catalysing effect.

U.S. Pat. No. 2,725,364 mentions that maleic acid or fumaric acid can be added onto 2-mercaptobenzothiazole at 30°–60° C. in aqueous-alkaline solution, but no experimental details are given.

However, attempts by the Applicant Company to add α,β-unsaturated carboxylic acids, in particular maleic acid and fumaric acid, onto 2-mercaptobenzothiazole in an alkaline-aqueous medium at 45°–50° C. have shown that no addition occurs within 100 hours. It is further known from A. F. Halasa et al. J.Org.Chem., Vol.36, 636–641(1971), that in reacting 2-mercaptobenzothiazole with activated olefins under alkaline reaction conditions the N-substituted benzothiazoline-2-thione derivatives are formed. Surprisingly, however, it has been found that the reaction of α,β-unsaturated carboxylic esters amides, imides and anhydrides with 2-mercaptobenzothiazole in a strongly acid medium proceeds under S-addition and the corresponding β-[benzothiazolyl-2-mercapto]-carboxylic acid derivatives are formed in fair yield and purity. The same applies to addition onto 2-mercaptobenzimidazole.

The invention thus relates to a process for the preparation of a compound of the formula I

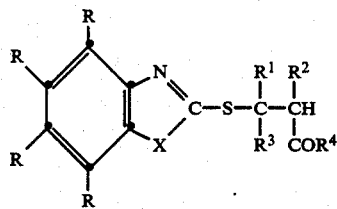

in which X is sulfur or NH, each radical R independently of the others is hydrogen, alkyl, halogenalkyl, alkoxy, alkylthio, alkylsulfonyl, phenyl, alkylphenyl, phenylalkyl, cycloalkyl, halogen, —NO$_2$, —CN, —COOH, —COOalkyl, or a tertiary amino or a carbamoyl group, R$^1$, R$^2$ and R$^3$ independently of one another are hydrogen, alkyl, halogenoalkyl, hydroxyalkyl, alkoxyalkyl, free or esterified carboxyl or carboxylalkyl, unsubstituted or substituted carbamoyl or carbamoylalkyl, or unsubstituted or substituted aryl or aralkyl, or R$^1$ and R$^2$ together are a direct bond or straight-chain or branched alkylene, which can be substituted by 1 or 2 carboxyl groups, R$^4$ is unsubstituted or substituted amino, alkoxy, cycloalkoxy, aryloxy, or aralkyloxy, or R$^2$ and R$^4$ together are —CH$_2$—CO—O— or —CH$_2$CO—NR$^5$— or R$^3$ and R$^4$ together are —CO—O— or —CO—NR$^5$—, forming an anhydride or an imide ring, wherein R$^5$ is unsubstituted or substituted alkyl, cycloalkyl, aryl aralkyl or hydrogen, by reaction of a mercaptan of the formula II

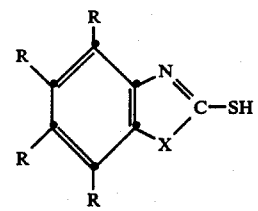

with an unsaturated carboxylic acid derivative of the formula III

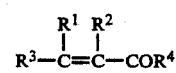

in a strongly acid medium.

An alkyl radical R in formulae I and II can be straight-chain or branched alkyl and is preferably C$_1$–C$_{12}$-alkyl, for example methyl, ethyl, propyl, isopropyl, n-butyl, isobutyl, tert.-butyl, pentyl, hexyl, octyl, nonyl, decyl or dodecyl. A halogenalkyl radical R is preferably C$_1$–C$_4$-halogenoalkyl, for example chloromethyl, mono-, di- or tri-fluoromethyl, trichloromethyl or 2-chloroethyl. An alkoxy or alkylthio radical R preferably has 1–4 carbon atoms and can be, for example, methoxy, ethoxy, isopropoxy, methylthio, propylthio or tert.-butylthio. An alkylsulfonyl radical R is preferably C$_1$–C$_{12}$-alkylsulfonyl and can be, for example, methylsulfonyl, tert.-butylsulfonyl, n-octylsulfonyl or n-dodecylsulfonyl.

A cycloalkyl radical R preferably contains 5–8 carbon atoms. Examples are cyclopentyl, cyclohexyl and cyclooctyl. An alkylphenyl or phenylalkyl radical R preferably has 7–12 carbon atoms and can be, for example, tolyl, xylyl, ethylphenyl, tert.-butylphenyl, benzyl, 1- or 2-phenylethyl or α,α-dimethylbenzyl. A —COOalkyl radical R is preferably —COO(C$_1$–C$_4$-alkyl), for example methoxycarbonyl, ethoxycarbonyl or butoxycarbonyl. A tertiary amino group or a carbamoyl group R is preferably such a group with up to 20 carbon atoms, for example —N(CH$_3$)$_2$, —N(C$_2$H$_5$)$_2$, —N(i—C$_3$H$_7$)$_2$, —N(CH$_2$CH$_2$OH)$_2$, —N(C$_4$H$_9$)$_2$, —(C$_8$H$_{17}$)$_2$, —N(CH$_3$)-phenyl, —CON(CH$_3$)-benzyl, piperidino, morpholino, —CONH$_2$, —CONCH$_3$, —CONHphenyl, —CON(CH$_3$)$_2$, —CON(C$_6$H$_{13}$)$_2$, morpholinocarbonyl or piperidino-carbonyl.

A compound of the formula II in which at least two of the substituents R are hydrogen, in particular compounds of the formula II in which one substituent R is hydrogen, C$_1$–C$_4$-alkyl, C$_1$–C$_4$-alkoxy, halogen or —COOH and the other three substituents R are hydrogen, are preferably used.

Compounds of the formula II in which X is sulfur are preferably used, and the corresponding β-(benzothiazol-2-ylthio)carboxylic acid derivatives are thereby obtained.

An alkyl substituent $R^1$, $R^2$ or $R^3$ in formulae I and III can be straight-chain or branched alkyl, in particular with 1–12 carbon atoms. Examples are methyl, ethyl, n-propyl, isopropyl, n-butyl, sec.-butyl, isobutyl, n-pentyl, isopentyl, hexyl, heptyl, octyl, nonyl, decyl and dodecyl. A halogenalkyl or hydroxyalkyl radical $R^1$, $R^2$ and $R^3$ preferably has 1–4 carbon atoms. Examples are hydroxylmethyl, 1- or 2-hydroxyethyl, 1- , 2- or 3-hydroxypropyl, 3-hydroxybutyl, chloromethyl, mono-, di- or tri-fluoromethyl, bromomethyl, 2-chloroethyl, 3-chloropropyl and 2-chlorobutyl.

An alkoxyalkyl radical $R^1$, $R^2$ or $R^3$ can be, in particular, $C_2$–$C_{10}$-alkoxyalkyl, for example methoxymethyl, 1- or 2-methoxyethyl, ethoxymethyl, 2-butoxyethyl or octyloxymethyl. A carboxyalkyl radical $R^1$, $R^2$ or $R^3$ can be, in particular, $C_2$–$C_{12}$-carboxyalkyl for example carboxymethyl, 1- or 2-carboxyethyl, 2- or 3-carboxypropyl, 1- or 4-carboxybutyl or 6-carboxyhexyl. The carboxyalkyl radical and the carboxyl radical may be esterified with an aliphatic or araliphatic alcohol. Said alcohol can be derived from the alkoxyresidues as defined for $R^4$. A carbamoylalkyl radical $R^1$, $R^2$ or $R^3$ can be, in particular, $C_2$–$C_{16}$-carbamoylalkyl for example 1- or 2-carbamoylethyl, 2- or 3-carbamoylpropyl, 1- or 4-carbamoylbutyl, 6-carbamoylhexyl, and especially carbamoylmethyl. The N-Atom of the carbamoyl or carbamoylalkyl groups may be substituted by aliphatic and/or aromatic radicals, having preferably 1 to 12 carbon atoms, for example alkyl, cycloalkyl, aryl or aralkyl, tetramethylen, pentamethylen or 3-oxapentylen. Examples are listed before for the carbamoyl-radical R. Preferably the N-atom is unsubstituted.

A substituted aryl or aralkyl radical $R^1$, $R^2$ or $R^3$ can be, in particular, phenyl or benzyl which is substituted by halogen, nitro, alkyl, hydroxyl, alkoxy or carboxyl, for example 4-chlorophenyl, 3-nitrophenyl, tolyl, xylyl, 4-tert.-butylphenyl, 4-hydroxyphenyl, 3-methoxyphenyl, 3- or 4-carboxyphenyl, 4-fluorobenzyl or 4-methylbenzyl.

If $R^1$ and $R^2$ together are a straight-chain or branched alkylene radical, they form together with the carbon atoms to which $R^1$ and $R^2$ are bonded a cycloalkane ring, preferably a cyclopentane or cyclohexane ring, which can be substituted by alkyl groups, preferably $C_1$–$C_4$-alkyl groups, or by one or two carboxyl groups.

Preferably, $R^1$, $R^2$ and $R^3$ independently of one another are hydrogen, $C_1$–$C_8$-alkyl, free or esterified carboxyl or $C_2$–$C_8$-carboxyalkyl, $C_2$–$C_8$-carbamoyl, $C_2$–$C_{16}$-carbamoylalkyl or phenyl, or $R^1$ and $R^2$ together are tri- or tetra-methylene. Particularly preferably, at least two or the substituents $R^1$, $R^2$ and $R^3$ are hydrogen.

If $R^4$ is an amino radical it preferably contains up to 20 carbon atoms and may be —$NH_2$ or a radical of the formula —$NR^6R^7$, wherein $R^6$ is $C_1$–$C_{12}$ alkyl, $C_6$–$C_{16}$-aryl, $C_7$–$C_{16}$aralkyl, $C_3$–$C_8$-cycloalkyl, $R^7$ is hydrogen or $R^7$ has the same meaning as $R^6$ or $R^6$ and $R^7$ together are $C_4$ to $C_8$-alkylene, which may be interrupted by oxygen. Preferably $R^6$ is $C_1$–$C_4$-alkyl.

$R^4$ as alkoxy radical can be, in particular, $C_1$–$C_{12}$-alkoxy and especially $C_1$–$C_6$-alkoxy, for example methoxy, ethoxy, propoxy, butoxy, pentoxy, hexoxy, octoxy or dodecyloxy. A cycloalkoxy radical $R^4$ can be, in particular, $C_5$–$C_8$-cycloalkoxy, for example cyclopentyloxy or cyclohexyloxy. An aryloxyradical $R^4$ can be, in particular, $C_6$- to $C_{16}$-aryloxy, for example phenoxy, methylphenoxy or chlorophenoxy. An aralkoxy radical $R^4$ can be, in particular, $C_7$–$C_{16}$-aralkoxy, for example benzyloxy or methylbenzyloxy.

$R^5$ as alkyl radical can be, in particular, $C_1$–$C_{12}$-alkyl, especially $C_1$–$C_4$-alkyl, for example methyl, ethyl, n-propyl, i-propyl, butyl, hexyl, octyl, dodecyl. A cycloalkyl radical $R^5$ can be for example cyclopentyl or cyclohexyl. An aryl radical $R^5$ can be, in particular, $C_6$–$C_{16}$-aryl, for example phenyl or methylphenyl. An aralkyl radical $R^5$ can be, in particular, $C_7$–$C_{16}$-aralkyl, for example benzyl.

The mercaptans of the formula II are known compounds or they can be prepared analogously to known compounds. Examples of compounds of the formula II which can be used according to the invention are: 2-mercaptobenzothiazole, 5-methyl-2-mercaptobenzothiazole, 4-isopropyl-2-mercaptobenzothiazole, 7-t-butyl-2-mercaptobenzothiazole, 6-cyclohexyl-2-mercapto-benzothiazole, 7-benzyl-2-mercapto-benzothiazole, 5-trifluoromethyl-2-mercaptobenzothiazole, 6-methoxy-2-mercapto-benzothiazole, 7-ethoxy-2-mercaptobenzothiazole, 4-methylthio-2-mercaptobenzothiazole, 6-methylsulfonyl-2-mercaptobenzothiazole, 4-fluoro-2-mercapto-benzothiazole, 5-chloro-2-mercapto-benzothiazole, 7-bromo-2-mercapto-benzothiazole, 6-chloro-2-mercapto-benzothiazole, 4-phenyl-2-mercapto-benzothiazole, 5-nitro-2-mercapto-benzothiazole, 5-cyano-2-mercapto-benzothiazole, 5-carboxy-2-mercapto-benzothiazole, 5-methoxycarbonyl-2-mercapto-benzothiazole, 7-hydroxy-2-mercapto-benzothiazole, 5-dimethylamino-2-mercapto-benzothiazole, 5-morpholino-2-mercapto-benzothiazole, 5-carbamyl-2-mercapto-benzothiazole, 5-phenylcarbamyl-2-mercapto-benzothiazole, 5-chloro-6-n-butyl-2-mercaptobenzothiazole, 5-nitro-6-n-propyl-2-mercapto-benzothiazole, 5-bromo-6-n-propoxy-2-mercapto-benzothiazole, 4,5,6-triethyl-2-mercapto-benzothiazole, 4,5,6,7-tetramethyl-2-mercaptobenzothiazole, 4-methoxy-6-hydroxy-2-mercapto-benzothiazole, 4,5-dimethyl-7-propoxy-2-mercapto-benzothiazole, 2-mercaptobenzimidazole, 6-methyl-2-mercapto-benzimidazole, 4-isopropyl-2-mercapto-benzimidazole, 5-n-hexyl-2-mercapto-benzimidazole, 6-(1,1,3,3-tetramethylbutyl)-2-mercapto-benzimidazole, 7-benzyl-2-mercapto-benzimidazole, 6-ethoxy-2-mercapto-benzimidazole, 6-isopropoxy-2-mercaptobenzimidazole, 4-fluoro-2-mercapto-benzimidazole, 5-chloro-2-mercapto-benzimidazole, 5-chloro-2-mercapto-benzimidazole, 5-cyano-2-mercapto-benzimidazole, 4-phenyl-2-mercapto-benzimidazole, 6-nitro-2-mercapto-benzimidazole, 5-carboxy-2-mercapto-benzimidazole, 5-butoxycarbonyl-2-mercapto-benzimidazole, 5-dimethylamino-, 4-piperidino-, 5-methylcarbamoyl or 5-diethylcarbamoyl-2-mercapto-benzimidazole, 4-bromo-5-n-hexyl-2-mercapto-benzimidazole, 5-nitro-6-npropyl-2-mercapto-benzimidazole, 4,5,6-triethyl-2-mercapto-benzimidazole and 4,5-dimethyl-7-propoxy-2-mercapto-benzimidazole.

The carboxylic acid derivative of the formula III is an ester, a partial ester, an amide, a partial amide, an imide or an anhydride. It can be derived for example from the following unsaturated carboxylic acids: acrylic acid, methacrylic acid, crotonic acid, 2,3- or 3,3-dimethylacrylic acid, propiolic acid, phenylpropiolic acid, maleic acid, fumaric acid, acetylene dicarboxylic acid, itaconic acid, cyclohexene-1,2-dicarboxylic acid, 3-methylcyclohexene-1,2-dicarboxylic acid, ethylenetetracarboxylic acid, mesaconic acid, glutaconic acid, aconitic acid, citraconic acid, α-methyleneglutaric acid, α-methyleneadipic acid, α-ethylidene-adipic acid, propylene-1,3-dicarboxylic acid, 1-butene-1,4-dicarboxylic acid, 1-butene-2,3,4-tricarboxylic acid, 2-pentenoic acid, 2-hexenoic acid, 2-octenoic acid, 2-decenoic acid, 2-undecenoic acid, 2-dedecenoic acid, 2-octadecenoic acid, cinnamic acid, α-phenylacrylic acid, α-phenylcrotonic acid, β-benzylacrylic acid, benzylidenemalonic acid, α-methylcinnamic acid, 4-chlorocinnamic acid and 3-nitrocinnamic acid.

When anhydrides are used, the reaction is carried out in anhydrous medium. The corresponding anhydride is first obtained, and can further easily be subsequently reacted to carboxylic acid derivatives of formula I. The anhydrides used as the reaction components are preferably those of 1,2-dicarboxylic acids. Examples of such anhydrides are maleic anhydride, itaconic anhydride and citraconic anhydride, as well as cyclohexene-1,2-dicarboxylic acid anhydride.

A dicarboxylic or polycarboxylic acid derivatives of the formula III in which $R^3$ is unesterified or esterified carboxyl or $R^2$ is unesterified or esterified carboxymethyl or carbamoylmethyl, or the cyclic anhydride of said acid is preferably used as the carboxylic acid derivative. Maleic acid derivatives are particularly preferably used.

The reaction of II with III is carried out in a strongly acid medium. The reaction medium can be, for example, an aqueous solution of a mineral acid, for example of $H_2SO_4$, $H_3PO_4$, HCl, HBr, $HBF_4$, $HClO_4$, $H_2S_2O_7$ or polyphosphoric acid. Organic acids, for example formic acid, trifluoroacetic acid or p-toluenesulfonic acids, can be used in aqueous solution or in organic solution. Certain acids can also serve as the reaction medium in undiluted form, for example trifluoroacetic acid, formic acid or phosphoric acid.

Lewis acids, for example $AlCl_3$, $AlBr_3$, $BR_3$, $SbF_5$, $SbCl_5$ or $SnCl_4$, can also be used as the acids. In this case, the reaction is carried out in an inert solvent in which the Lewis acids is soluble, for example in diethyl ether or in halogenated hydrocarbons.

If the starting materials are insoluble in the aqueous acid used, it is also possible to add a water-miscible organic solvent, for example methanol, ethanol, ethylene glycol monomethyl ether, acetic acid, propionic acid, tetramethylenesulfone (sulfolane), tetrahydrofuran, dioxane, acetone or dimethylsulfoxide. In this case, the reaction is thus carried out in an acid aqueous-organic medium.

The reaction is preferably carried out in an aqueous or aqueous-organic solution of a strong proton acid, in particular in 60–90% sulfuric acid or in 25–38% hydrochloric acid.

The reaction temperature can be in the range from −30° C. up to the boiling point of the reaction medium, and is preferably 0° to 100° C., in particular 0°–50° C. Under certain conditions, it may be advantageous to carry out the reaction under increased pressure, but this is not necessary.

The reaction components are used in the approximate molar ratio of 1:1, a slight excess of up to about 10 mol% of the carboxylic acid derivative III being employed. One component can first be dissolved or dispersed in the acid reaction medium and the second component can then be added. Alternatively, the two components are first mixed and this mixture is introduced slowly into the acid reaction medium.

The products can be isolated by customary methods. If a concentrated mineral acid is used, it is advantageous to dilute the reaction mixture with water after the reaction has finished and to neutralise some of the mineral acid by addition of a base, such as NaOH or $NaCO_3$, in which case the product usually precipitates after cooling or can be isolated by extraction. The crude product can be purified by reprecipitation. In general, the products precipitate in high purity by the process according to the invention, so that further purification is frequently unnecessary. Position isomers may be obtained, when dicarboxylic derivatives are used, having different acid and/or acid derived groups, for example a carboxylic and an ester group.

The compounds of the formula I can be used as corrosion inhibitors in aqueous systems or in coatings for metals. The invention is illustrated in more detail by the following examples. The temperatures in the examples are given in °C.

EXAMPLE 1

16.8 g of finely powdered 2-mercaptobenzothiazole are suspended in 120 ml of 70% sulfuric acid, and 25.3 g of dibutyl maleate are added dropwise at 0°–10° in the course of half an hour, with stirring. After further 5 hours at 0°–10°, the reaction mixture is poured into ice water and extracted with acetic ethyl acetate. The organic phase is separated and the solvent is evaporated. There yields 32 g rough product, which is purified by filtration of an ethyl acetate/hexane (1:3) solution over silica gel. The obtained dibutyl benzothiazol-2-ylthiosuccinate is a yellowish oil ($n_D^{20}=1,5515$).

Analysis ($C_{19}H_{25}NO_4S_2$). calculated: 57.7 %C, 6.4 %H, 16.2 %O, 16.2 %S. found: 57.6 %C, 6.6 %H, 16.5 %O, 15.5 %S.

The same reaction is carried out with diethyl maleate and diethyl fumarate. There is obtained diethyl benzothiazol-2-ylthiosuccinate as yellowish oil ($n_D^{20}=1,5765$)

Analysis ($C_{15}H_{17}NO_4S_2$). calculated: 53.08 %C, 5.05 %H, 4.13 %N, 18.86 %O, 18.89 %S. found: 53.2 %C, 5.0 %H, 4.1 %N, 19.1 %O, 18.7 %S.

EXAMPLE 2

16.8 g of finely powdered 2-mercaptobenzothiazole are suspended in 150 ml of 70% sulfuric acid and 16.6 g of dimethyl itaconate are added dropwise at 0°–10° in the course of half an hour, with stirring. After further 16 hours at 0°–10°, the reaction mixture is poured into ice water and extracted with ethyl acetate. The organic phase is separated, dried and the solvent is evapourated. The solid residue is recristallied from cyclohexane yielding dimethyl 3-(benzothiazol-2-ylthio)-propane-1,2-dicarboxylate, melting at 46°–47°.

Analysis ($C_{14}H_{15}NO_4S_2$). calculated: 51.68 %C, 4.65 %H, 4.31 %N, 19.71 %S. found: 51.8 %C, 4.7 %H, 4.2 %N, 19.5 %S.

EXAMPLE 3

16.8 g of finely powdered 2-mercaptobenzothiazole are suspended in 130 ml 70% sulfuric acid and 11.0 g of ethyl acrylate are added dropwise at 1°–10° in the course of 1 hour, with stirring. After further 1.5 hours at 0°–10°, the reaction mixture is poured into ice water and extracted with ethyl acetate. The organic phase is separated and the solvent is evaporated. There yields 18.3 g of liquid ethyl 3-(benzothiazol-2-ylthio)propionate, $n_D^{20}=1,6120$.

Analysis (C$_{12}$H$_{13}$NO$_2$S$_2$). calculated: 53.91 %C, 4.90 %H, 5.24 %N, 11.97 %O, 23.98 %S. found: 53.6 %C, 4.9 %H, 5.3 %N, 12.0 %O, 24.0 %S.

EXAMPLE 4

16.8 g of finely powdered 2-mercaptobenzothiazole are suspended in 75 ml 70% sulfuric acid and 12.0 g of ethyl crotonate are added dropwise at 0°–10° in the course of 1 hour. After further 5 hours at 0°–10°, the reaction mixture is poured into ice water and extracted with ethyl acetate. The organic phase is separated and the solvent is evaporated. There yield 26.1 g of a liquid, which is purified according to example 1. There is obtained 17.1 g of ethyl 3-(benzothiozol-2-ylthio)-butyrate, $n_D^{20} = 1,5965$.

Analysis (C$_{13}$H$_{15}$NO$_2$S$_2$). calculated: 55.49 %C, 5.37 %H, 4.98 %N, 11.37 %O, 22.79 %S. found: 55.7 %C, 5.4 %H, 5.0 %N, 11.4 %O, 22.5 %S.

EXAMPLE 5

A finely powdered mixture of 16.8 g of 2-mercaptobenzothiazole and 7.5 g of acrylic amide are added at 45°–50° in the course of 1 hour to 100 ml 70% sulfuric acid, with stirring. After a further hour at 45°–50°, the reaction mixture is poured into ice water. The precipitate is filtered off, washed with water and dried. There yield 22.1 g of 2-(benzothiazol-2-ylthio)-propionic acid amide, which melts at 144°–145° C. after recrystallisation from ethyl acetate.

Analysis (C$_{10}$H$_{10}$N$_2$OS$_2$). calculated: 50.40 %C, 4.23 %H, 11.76 %N, 26.91 %S. found: 50.2 %C, 4.3 %H, 11.6 %H, 26.6 %S.

EXAMPLE 6

A finely powdered mixture of 16.8 g (0.1 mol) of 2-mercaptobenzothiazole and 15.1 g (0.105 mol) of monoethyl fumarate are added at 0°–5° in the course of 1 hour to 150 ml 70% sulfuric acid. After further 5 hours at 0°–10°, the reaction mixture is poured into ice water and extracted with ethyl acetate. The organic phase is separated and the solvent is evaporated yielding 22.8 g rough product, which is purified according to example 1. There is obtained an isomer mixture of (benzothiazol-2-yl-thio)-succinic acid monoethyl ester as sticky mass.

| Analysis (C$_{13}$H$_{13}$NO$_4$S$_2$) | | | | |
|---|---|---|---|---|
| calculated: | 50.4% C | 4.2% H | 4.5% N | 20.9% S |
| found: | 50.2% C | 4.3% H | 4.6% N | 20.6% S |

EXAMPLE 7

13.7 g (0.105 mol) of monoethyl maleinate are dropped to a stirred suspenesion of 16.8 g (0.1 mol) of 2-mercaptobenzothiazole in 100 ml 70% sulfuric acid at 0°–5°. After 5 hours stirring at 10° the reaction mixture is poured onto ice and the ice water is extracted by ethyl acetate. After evaporation of the organic solution there remain 29.8 g of a mixture of the two isomeric monoethyl (benzothiazol-2-ylthio)-succinates. The product is dissolved in ethyl acetate/methanol 9:1 and the solution is filtered over silica and the thus obtained main isomer is recrystallised from ethyl acetate yielding a compound melting at 87°–89°.

| Analysis (C$_{12}$H$_{11}$NO$_4$S$_2$) | | | | |
|---|---|---|---|---|
| calculated: | 48.5% C | 3.7% H | 4.7% N | 21.6% S |
| found: | 47.8% | 3.7% | 4.6% | 21.0% |

EXAMPLE 8

15 g (0.105 mol) of dimethyl acetylene-dicarboxylate are dropped within 1 hour to a stirred suspension of 16.8 g (0.1 mol) 2-mercaptobenzothiazole in 200 ml of 70% sulfuric acid at 10° C. After 16 hours stirring at 20°–25° C. the reaction mixture is poured onto ice. The ice water is extracted by ethyl acetate. The organic solution is dried over Na$_2$SO$_4$ and evaporated. The residue (27 g) is a mixture of the two isomeric monomethyl (benzothiazol-2-ylthio)maleinates. By recrystallisation from ethyl acetate one isomer melting at 144° could be obtained.

| Analysis (C$_{12}$H$_9$NO$_4$S$_2$) | | | | |
|---|---|---|---|---|
| calculated: | 48.8% C | 3.1% H | 4.7% N | 21.7% S |
| found: | 48.8% | 3.2% | 4.5% | 21.1% |

EXAMPLE 9

26 g (0.105 mol) 1,2-diethyl 3-methyl 4-butene-1,2,3-tricarboxylate are dropped to a stirred suspension of 16.4 g (0.1 mol) 2-mercaptobenzothiazole in 160 ml 70% sulfuric acid. After 16 hours stirring at 20°–25° the reaction mixture is poured onto ice and extracted by dichloromethane. The raw product obtained by evaporation of the organic solution is purified by column-chromatography over silica yielding the 4-(benzothiazol-2-ylthio)-butane 3-methylcarboxylate 1,2-diethyldicarboxylate as a viscous oil.

NMR (250 MH$_Z$, CDCl$_3$): 1.25(6H), 2.7(1H), 3.0(1H), 3.45(5H), 3.75 (4H), 4.2(2H), 7.35(2H), 7.8(2H).

What is claimed is:

1. A process for the preparation of a compound of the formula I

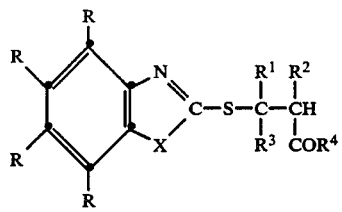

in which X is sulfur or NH, each radical R independently of the others is hydrogen, alkyl, halogenalkyl, alkoxy, alkylthio, alkylsulfonyl, phenyl, alkylphenyl, phenylalkyl, cycloalkyl, halogen, NO$_2$, —CN, —COOH, —COOalkyl or a tertiary amino or a carbamoyl group and R$^1$, R$^2$ and R$^3$ independently of one another are hydrogen, alkyl, halogenoalkyl, hydroxyalkyl, alkoxyalkyl, free or esterified carboxyl or carboxylalkyl, unsubstituted or substituted carbamoyl or carbamoylalkyl, or unsubstituted or substituted aryl or aralkyl, or R$^1$ and R$^2$ together are a direct bond or straight-chain or branched alkylene, which can be substituted by 1 or 2 carboxyl groups, R$^4$ is unsubstituted or substituted amino, alkoxy, cycloalkoxy, aryloxy or aralkyloxy, or R$^2$ and R$^4$ together are —CH- $_2$—CO—O— or —CH$_2$CO—NR$^5$— or R$^3$ and R$^4$ together are —CO—O— or —CO—NR$^5$—, forming an anhydride or an imide ring, wherein R$^5$ is unsubstituted or substituted alkyl, cycloalkyl, aryl, aralkyl or hydrogen, by reaction of a mercaptan of the formula II

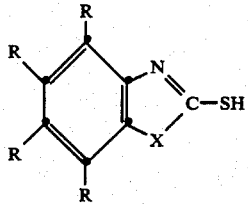

with an unsaturated carboxylic acid derivative of the formula III

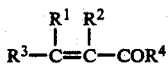

in a strongly acid medium.

2. A process according to claim 1, wherein the reaction medium is an aqueous or organic-aqueous solution of a strong proton acid.

3. A process according to claim 2, wherein the reaction medium is 60–90% sulfuric acid or 25–38% hydrochloric acid.

4. A process according to claim 1, wherein the reaction is carried out at a temperature of 0° C. to 100° C.

5. A process according to claim 1, wherein a mercaptan of the formula II is used in which at least two of the substituents R are hydrogen.

6. A process according to claim 5, wherein one of the radicals R is hydrogen, C$_1$–C$_4$-alkyl, C$_1$–C$_4$-alkoxy, halogen or —COOH and the other three radicals R are hydrogen.

7. A process according to claim 1, wherein a compound of the formula II is used in which X is sulfur.

8. A process according to claim 1, wherein a carboxylic acid derivative of the formula III is used in which R$^1$, R$^2$ and R$^3$ independently of one another are hydrogen, C$_1$–C$_8$-alkyl, C$_2$–C$_8$-carbamoyl or C$_2$–C$_{16}$-carbamoylalkyl, free or esterified carboxyl or C$_2$–C$_8$-carboxyalkyl, or phenyl, or R$^1$ and R$^2$ together are tetramethylene, and R$^4$ is amino containing up to 20 carbon atoms, C$_1$–C$_{12}$-alkoxy, C$_5$–C$_8$-cycloalkoxy, C$_6$–C$_{16}$-aryloxy or C$_7$–C$_{16}$-aralkyloxy, or R$^2$ and R$^4$ together are —CH$_2$CO—NR$^5$— or R$^3$ and R$^4$ together are —CO—NR$^5$—, wherein R$^5$ is C$_1$–C$_{12}$-alkyl, C$_5$–C$_8$-cycloalkyl, C$_6$–C$_{16}$-aryl, C$_7$–C$_{16}$-aralkyl or hydrogen.

9. A process according to claim 1, wherein a carboxylic acid derivative of the formula III is used in which at least two of the substituents R$^1$, R$^2$ and R$^3$ are hydrogen.

10. A process according to claim 1, wherein a carboxylic acid derivative of the formula III is used in which R$^3$ is free or esterified carboxyl or carbamoyl, or R$^2$ is free or esterified carboxymethyl or carbamoylmethyl.

11. A process according to claim 10, wherein a compound of the formula II is reacted with a maleic acid derivative or an itaconic acid derivative in a strongly acid medium.

12. A process, according to claim 1, wherein R$^4$ in formula I is C$_1$–C$_6$-alkoxy, cyclohexyloxy, cyclopentyloxy, phenyloxy, benzyloxy, —NH$_2$ or —NR$^6$R$^7$, wherein R$^6$ is C$_1$–C$_4$-alkyl and R$^7$ is hydrogen or C$_1$–C$_4$-alkyl.

13. A process according to claim 1, wherein R$^5$ is C$_1$–C$_4$-alkyl, cyclohexyl, phenyl, benzyl or hydrogen.

* * * * *